US010279113B2

(12) United States Patent
Brouillette et al.

(10) Patent No.: US 10,279,113 B2
(45) Date of Patent: May 7, 2019

(54) NEEDLELESS SYRINGE AND METHOD FOR DELIVERING THERAPEUTIC PARTICLES

(71) Applicant: SOCPRA SCIENCES ET GÉNIE S.E.C., Sherbrooke (CA)

(72) Inventors: Martin Brouillette, Sherbrooke (CA); Christian Hebert, Sherbrooke (CA)

(73) Assignee: SOCPRA SCIENCES ET GENIE S.E.C., Sherbrooke (CA)

( * ) Notice: Subject to any disclaimer, the term of this patent is extended or adjusted under 35 U.S.C. 154(b) by 0 days.

(21) Appl. No.: 14/891,450

(22) PCT Filed: May 14, 2014

(86) PCT No.: PCT/CA2014/050453
§ 371 (c)(1),
(2) Date: Nov. 16, 2015

(87) PCT Pub. No.: WO2014/183216
PCT Pub. Date: Nov. 20, 2014

(65) Prior Publication Data
US 2016/0089496 A1    Mar. 31, 2016

Related U.S. Application Data

(60) Provisional application No. 61/824,651, filed on May 17, 2013.

(51) Int. Cl.
*A61M 5/30* (2006.01)
*A61M 37/00* (2006.01)
*A61M 5/20* (2006.01)

(52) U.S. Cl.
CPC ......... *A61M 5/3015* (2013.01); *A61M 5/2053* (2013.01); *A61M 2037/0007* (2013.01)

(58) Field of Classification Search
CPC .... A61M 5/3015; A61M 5/30; A61M 5/3007; A61M 5/2053; F41A 21/28; B41J 2/01; B41J 2/015; B41J 2/07
USPC .......................................................... 604/70
See application file for complete search history.

(56) References Cited

U.S. PATENT DOCUMENTS

| 5,630,796 A * | 5/1997 | Bellhouse ........... A61M 5/3015 604/518 |
| 5,811,714 A | 9/1998 | Hull et al. |
| 5,899,880 A * | 5/1999 | Bellhouse .............. C12M 35/04 222/389 |
| 6,592,545 B1 * | 7/2003 | Bellhouse ........... A61M 5/3015 604/141 |

(Continued)

FOREIGN PATENT DOCUMENTS

| WO | 00/10630 A1 | 3/2000 |
| WO | 01/47586 A1 | 7/2001 |

(Continued)

*Primary Examiner* — Nathan R Price
*Assistant Examiner* — John A Doubrava
(74) *Attorney, Agent, or Firm* — BCF LLP

(57) ABSTRACT

The present disclosure relates to a needleless syringe and method for delivering therapeutic particles. A source of therapeutic particles is located between a gas source and a cannon having a side opening. Gas released from the gas source causes a propagation of the therapeutic particles through the cannon. The side opening causes a reduction of a pressure of the gas in the cannon.

13 Claims, 19 Drawing Sheets

(56) References Cited

U.S. PATENT DOCUMENTS

| | | | | |
|---|---|---|---|---|
| 6,782,651 B1 * | 8/2004 | Walker | ................... | F41C 27/00 |
| | | | | 42/79 |
| 7,060,048 B1 * | 6/2006 | Nat | ................... | A61M 5/3015 |
| | | | | 604/500 |
| 7,073,426 B1 | 7/2006 | White | | |
| 7,320,677 B2 | 1/2008 | Brouillette | | |
| 7,909,793 B2 * | 3/2011 | Kendall | .............. | A61M 5/3015 |
| | | | | 604/207 |
| 2002/0091353 A1 * | 7/2002 | Bellhouse | ........... | A61M 5/3015 |
| | | | | 604/68 |
| 2002/0100361 A1 * | 8/2002 | Russell | .................... | F41A 1/00 |
| | | | | 89/14.5 |
| 2004/0215135 A1 * | 10/2004 | Sheldrake | ........... | A61M 5/3015 |
| | | | | 604/68 |
| 2004/0255447 A1 * | 12/2004 | Kendall | .............. | A61M 5/3015 |
| | | | | 29/428 |
| 2010/0121262 A1 * | 5/2010 | Bates | ................... | A61M 5/204 |
| | | | | 604/71 |
| 2010/0298767 A1 * | 11/2010 | Bates | ................. | A61M 5/2459 |
| | | | | 604/72 |

FOREIGN PATENT DOCUMENTS

| | | |
|---|---|---|
| WO | 01/51109 A1 | 7/2001 |
| WO | 01/68167 A1 | 9/2001 |

* cited by examiner

NEEDLELESS SYRINGE AND METHOD FOR DELIVERING THERAPEUTIC PARTICLES

TECHNICAL FIELD

The present disclosure relates to the field of needleless syringes. More specifically, the present disclosure relates to a needleless syringe and to a method for the subcutaneous delivery of therapeutic agents.

BACKGROUND

In a broad sense, needleless syringes are used for the subcutaneous injection of therapeutic agents. Conventional needleless syringes rely on rapid expansion of a gas to accelerate a flow of the therapeutic agents in particle form. Use of a needleless syringe avoids physically perforating the epidermis. The therapeutic agents can present themselves in powder form. The active substances can be vaccines, anesthetics, medicines, hormones, and genetic compounds, for example. These agents, while in the form of particles whose size is of the order of a few microns to tens of microns, are capable of penetrating the skin of a patient, due to the high velocity imparted upon them.

Conventional needleless syringes may fail to meet some of the required characteristics for such devices. Penetration depth of the therapeutic agents may not be sufficient for some applications. Penetration depth versatility is therefore lacking.

Therefore, there is a need for needleless syringes having improved operational characteristics.

SUMMARY

According to the present disclosure, there is provided a needleless syringe for delivering therapeutic particles. The needleless syringe comprises a gas source, a cannon having a side opening, and a source of therapeutic particles located between the gas source and the cannon. Gas released from the gas source causes a propagation of the therapeutic particles through the cannon. The side opening is configured to reduce a pressure of the gas in the cannon.

Figures 30, 31:
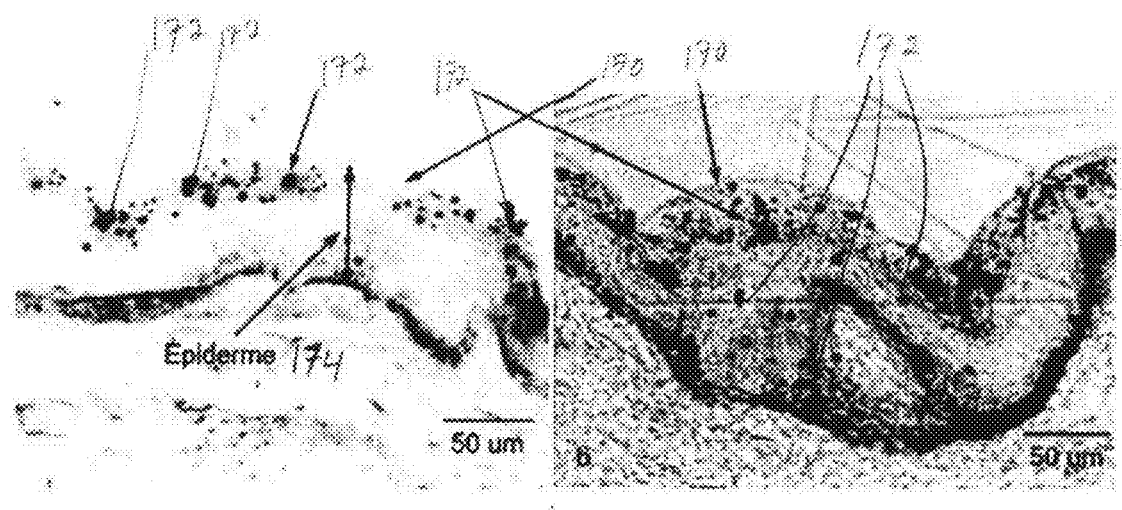

According to the present disclosure, there is also provided a method for delivering therapeutic particles to a skin surface. A gas source and a cannon having a side opening are provided. A source of therapeutic particles is placed between the gas source and the cannon. Gas is released from the gas source to cause a propagation of the therapeutic particles through the cannon. A pressure of the gas in the cannon is reduced by a configuration of the side opening.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which:

FIG. 1 is a front right perspective view of a conventional needleless syringe;

FIG. 2 is a front right perspective and exploded view of the conventional needleless syringe of FIG. 1;

FIG. 3 is a right side elevation view of the conventional needleless syringe of FIG. 1;

FIG. 4 is a right side elevation, cutaway view of the conventional needleless syringe of FIG. 1;

FIG. 5 is a schematic representation of a movement of particles within the cannon of the conventional needleless syringe of FIG. 1;

FIG. 6 is a front right perspective and exploded view of a needleless syringe having a slotted cannon;

FIG. 7 is a right side elevation, cutaway view of the needleless syringe of FIG. 6;

FIG. 8 is a right side elevation, cutaway view of a variant of a needleless syringe having a shorter external tube;

FIG. 9 is a right side elevation view of a theoretical, ideal cannon for the needleless syringe of FIG. 6;

FIG. 10 is a right side elevation view of an actual cannon prototype made for the needleless syringe of FIG. 6;

FIG. 11 is a front right perspective view of the cannon of FIG. 10;

FIG. 12 is a left side elevation view of the cannon of FIG. 10;

FIG. 13 is a front elevation view of the cannon of FIG. 10;

FIG. 14 is a sectional view of the cannon of FIG. 10 taken along lines E-E of FIG. 12;

FIG. 15 is a front right perspective, partial cutaway view of a first variant of a cannon having structural stiffeners that provide defining fully circular slots;

FIG. 16 is a front right perspective view of a second variant of a cannon having structural stiffeners that are imbedded in a tube;

FIG. 17 is a front right perspective view of a helicoidal cannon variant;

FIG. 18 is a right side elevation view of the helicoidal cannon of FIG. 17;

FIG. 19 is a schematic illustration of a gas flow near a transversal slot of a needleless syringe cannon;

FIG. 20 schematically shows an effect of a width of the slot of the slotted cannon of a needleless syringe;

FIG. 21 is a schematic representation of particles inside the needleless syringe having a cannon with a single transversal slot, at the time of release of a gas;

FIG. 22 is a schematic representation of particles inside the needleless syringe of FIG. 21, at 100 μs after release of the gas;

FIG. 23 is a schematic comparison of particle movement and flow properties within the conventional needleless syringe of FIG. 1 and within the needleless syringe of FIG. 6, at 95 μs after release of the gas;

FIG. 24 is a schematic comparison of particle movement and flow properties within the conventional needleless syringe of FIG. 1 and within the needleless syringe of FIG. 6, at 125 μs after release of the gas;

FIG. 25 is a schematic comparison of particle movement and flow properties within the conventional needleless syringe of FIG. 1 and within the needleless syringe of FIG. 6, at 128 μs after release of the gas;

FIG. 26 is a schematic comparison of particle movement and flow properties within the conventional needleless syringe of FIG. 1 and within the needleless syringe of FIG. 6, at 150 μs after release of the gas;

FIG. 27 is a graph showing an effect on gas flow velocity obtained from a single transversal slot on a needleless syringe cannon;

FIG. 28 is a graph showing an effect on gas flow velocity obtained from plural transversal slots on a needleless syringe cannon;

FIG. 29 is a graph showing an effect on gas pressure obtained from by plural transversal slots on a needleless syringe cannon;

FIG. 30 is a transversal microphotograph of human skin, showing a particle depth following injection using a conventional needleless syringe; and FIG. 31 is a transversal microphotograph of human skin, showing a particle depth following injection using the needleless syringe of FIG. 6.

Like numerals represent like features on the various drawings.

DETAILED DESCRIPTION

Various aspects of the present disclosure generally address one or more of the problems related to operational characteristics of conventional needleless syringes. As disclosed herein, a needleless syringe for delivering therapeutic particles comprises a gas source, a cannon, and a source of therapeutic particles located between the gas source and the cannon. The cannon has at least one side opening and may have plural side openings along its length. Releasing gas from the gas source causes a propagation of the therapeutic particles through the cannon. A local acceleration of a flow of the gas in the cannon, in the vicinity of the side opening, and a reduction of a gas pressure within the cannon are effected by the presence of the side opening on the cannon.

Figures 1, 2:
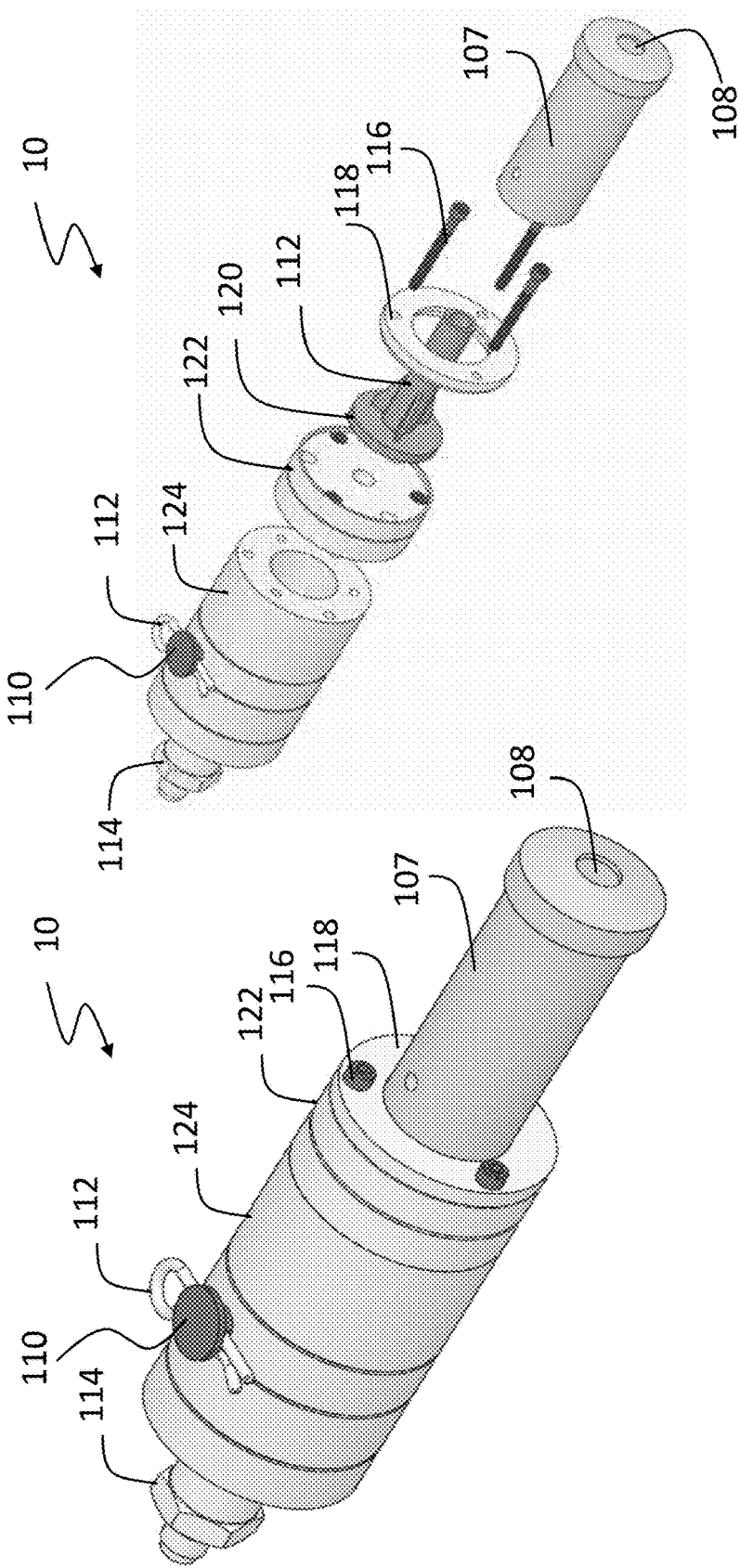
Figure 3:
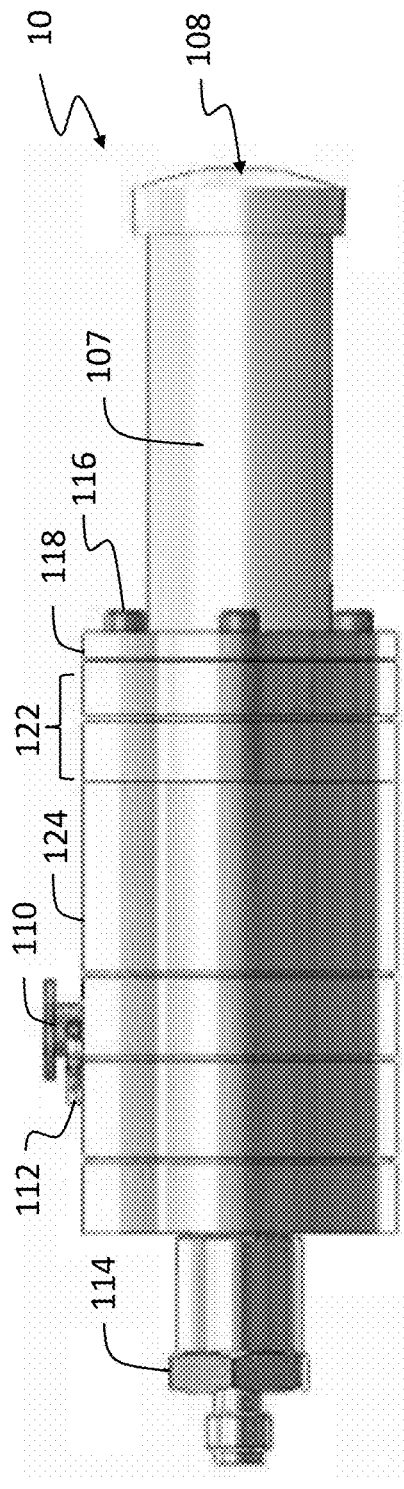
Figure 4:
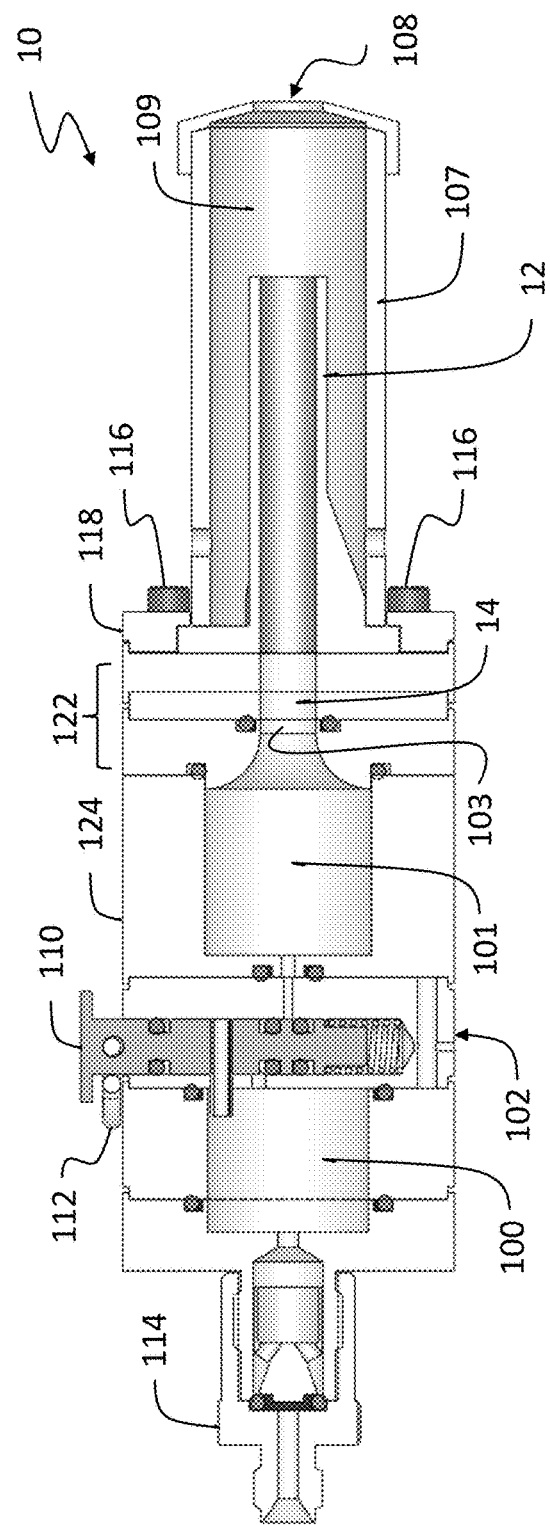

Referring now to the drawings, FIG. 1 is a front right perspective view of a conventional needleless syringe. FIG. 2 is a front right perspective and exploded view of the conventional needleless syringe of FIG. 1. FIG. 3 is a right side elevation view of the conventional needleless syringe of FIG. 1. FIG. 4 is a right side elevation, cutaway view of the conventional needleless syringe of FIG. 1. Referring at once to FIGS. 1-4, a needleless syringe 10 comprises a gas reservoir 100, a secondary reservoir, also called driver 101, a valve 102 separating the gas reservoir 100 and the driver 101, the gas reservoir 100, the driver 101 and the valve 102 collectively form a gas source. The needleless syringe 10 also comprises a puncturable membrane 103 separating the driver 101 from a source of therapeutic particles 14, a cannon 12, and an optional tube 107 positioning the cannon 12 in relation to an injection site 108. An actuator 110 triggers opening of the valve 102 so that gas from the gas reservoir 100 fills the driver 101 at a pressure sufficient to break the puncturable membrane 103, thereby causing a gas flow in the cannon 12, the gas flow carrying the therapeutic particles 14 towards the injection site 108. A safety pin 112 prevents accidentally depressing the actuator 110. A fill valve 114 allows charging the gas reservoir 100 before use. Screws 116 are used for mounting the needleless syringe 10 by attaching a ring 118 holding the tube 107 and a base 120 the cannon 12 onto a disc 122 that contains the puncturable membrane 103 and the therapeutic particles 14, the disc 122 itself being mounted using the screw 116 on a main body 124 of the needleless syringe 10. When present, the tube 107 surrounds the cannon 12. As illustrated, a length of the tube 107 extends beyond a length of the cannon 12, forming an exit area 109. The tube 107 provides a standoff distance between the injection site 108 and a point of exit of the cannon 12. Presence of the tube 107 surrounding the cannon 12 also helps in reducing noise produced by the gas upon actuation of the needleless syringe 10. The tube 107 may be omitted in a variant of the needleless syringe 10.

Figure 5:
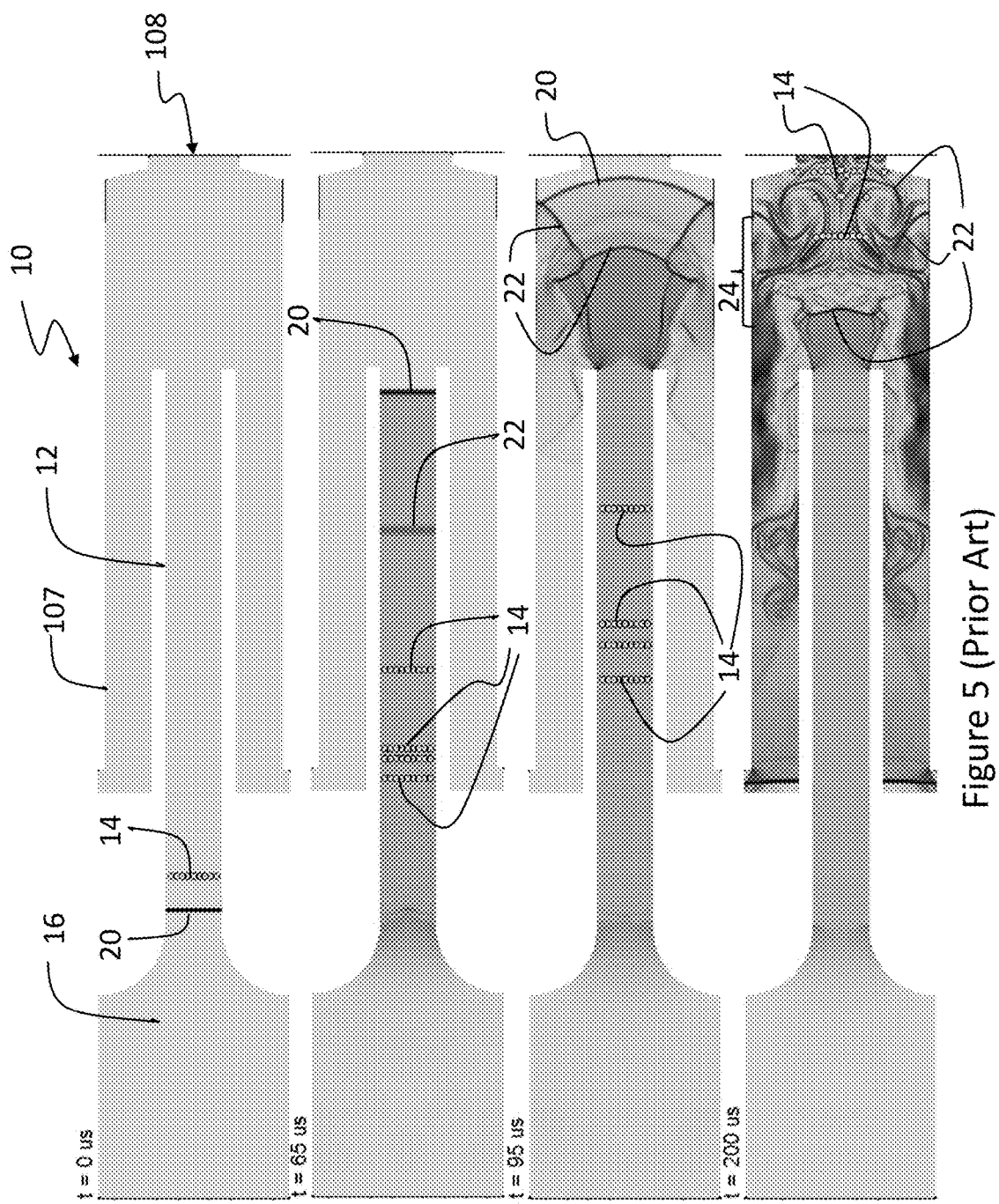

FIG. 5 is a schematic representation of a movement of particles within the cannon of the conventional needleless syringe of FIG. 1. The conventional needleless syringe 10 is represented at a time t=0 μs, which is a time of release of a gas from a gas source 16 in the cannon 12 enclosed within the tube 107, and then at 65, 95 and 200 μs thereafter. A shock wave 20 is initiated at time t=0, caused by an important gas pressure discontinuity between the gas source 16 and the cannon 12. The shock wave 20 then propagates at a constant velocity along the cannon 12, creating a flow of gas inside the cannon. A charge of therapeutic particles 14 advances in the cannon 12, dragged, i.e., entrained, by the gas flow. The particles 14 are mostly at or near the injection site 108 of the conventional needleless syringe 10 at time t=200 μs. Various flow density waves 22 illustrate a large lack of uniformity of a gas flow within the conventional needleless syringe 10. When the shock wave 20 reaches a subject's skin at the injection site 108, it is reflected again within the conventional needleless syringe 10 and creates a zone 24 in which a local flow density is large while a velocity of the flow is drastically reduced, and may even be negative, whereby a large pocket of gas going in the opposite direction may be created. This phenomenon slows down the particles 14 and reduces operational performance of the conventional needleless syringe 10. Some of the particles 14 may actually fail to reach the injection site 108.

FIG. 6 is a front right perspective and exploded view of a needleless syringe having a slotted cannon. FIG. 7 is a right side elevation, cutaway view of the needleless syringe of FIG. 6. Referring at once to FIGS. 6 and 7, a needleless syringe 99 comprises many elements of the conventional needleless syringe 10, including the gas reservoir 100, the secondary reservoir or driver 101, valve 102, the puncturable membrane 103, the source of therapeutic particles 14, the actuator 110, the safety pin 112, the fill valve 114, the screws 116, the ring 118, the disc 122, the main body 124, and the optional tube 107, these elements being assembled as described in the foregoing description of FIG. 1-4. The cannon 12 of the conventional needleless syringe 10 is substituted with a cannon 105 having plural side openings shaped as transversal slots 106. Variants of the cannon 105 having a single transversal slot 106, or a larger or smaller number of transversal slots 106, or different slot shapes, can also be contemplated. FIG. 8 is a right side elevation, cutaway view of a variant of a needleless syringe having a shorter external tube. As shown on FIG. 8, a tube 107' may be tailored so that its extremity matches an extremity of the cannon 105, at an injection site 108'.

Externally, the needleless syringe of FIG. 6 is visually similar, or identical, to the conventional needleless syringe as shown on FIGS. 1 and 3; an exception to this occurs in variants without the optional tube 107, in which the transversal slots 106 of the cannon 105 are visible.

When present, the tube 107 surrounds the cannon 105, positions the cannon 105 in relation to the injection site 108, and has an internal diameter that provides sufficient clearance for allowing release of gas from the cannon 105 through the transversal slots 106. Presence of the tube 107 surrounding the cannon 105 helps in reducing noise produced by the gas upon actuation of the needleless syringe 99. As illustrated, a length of the tube 107 extends beyond a length of the cannon 105, forming an exit area 109.

The needleless syringe 99 and the conventional needleless syringe 10 are operated similarly. However, presence of the transversal slots 106 on the cannon 105 impacts the performance of the needleless syringe 99. The following paragraphs will describe how the transversal slots influence a flow of gases within the cannon 105.

FIG. 9 is a right side elevation view of a theoretical, ideal cannon for the needleless syringe of FIG. 6. An ideal cannon 105*a* is divided into a plurality of floating rings 115 separated by slots 106. The ideal cannon 105*a* cannot be realized in practice. Regardless, any practical variation of the ideal cannon 105a is within the scope of the present disclosure. The following lines will describe actual cannon prototypes.

Figure 6:
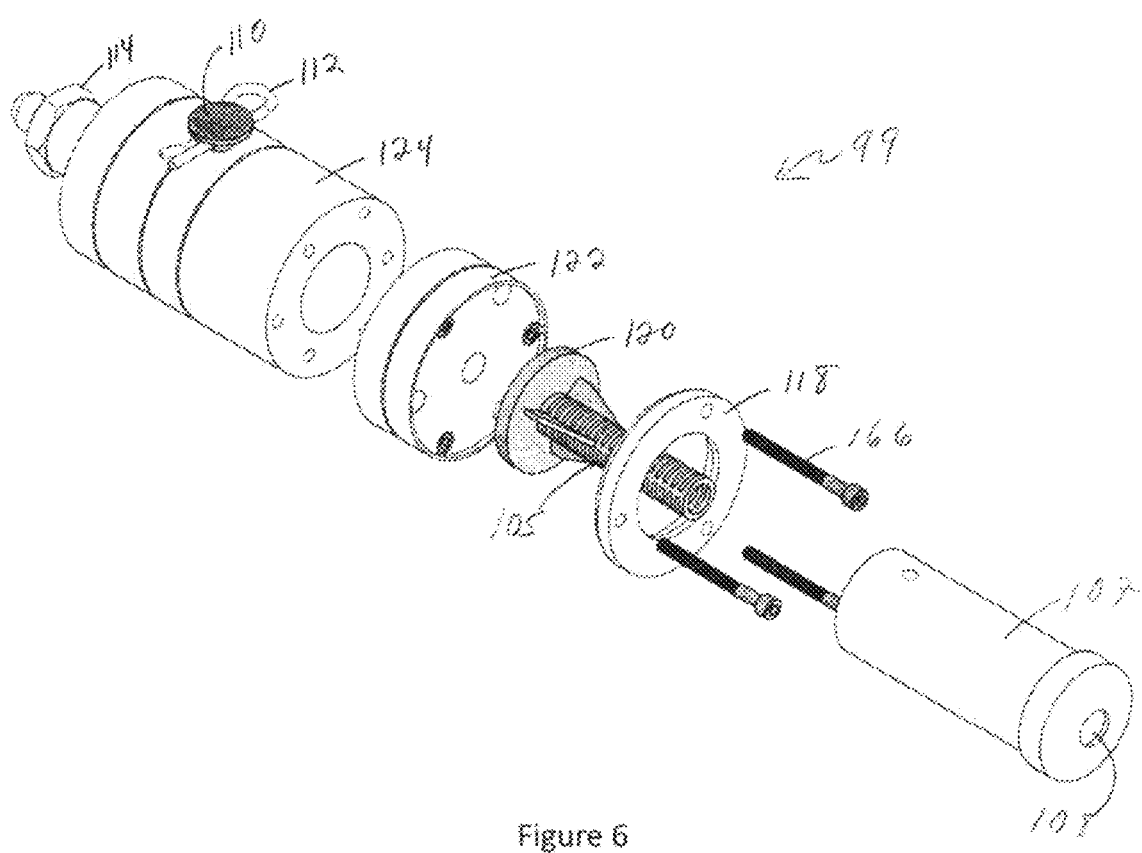
Figure 7:
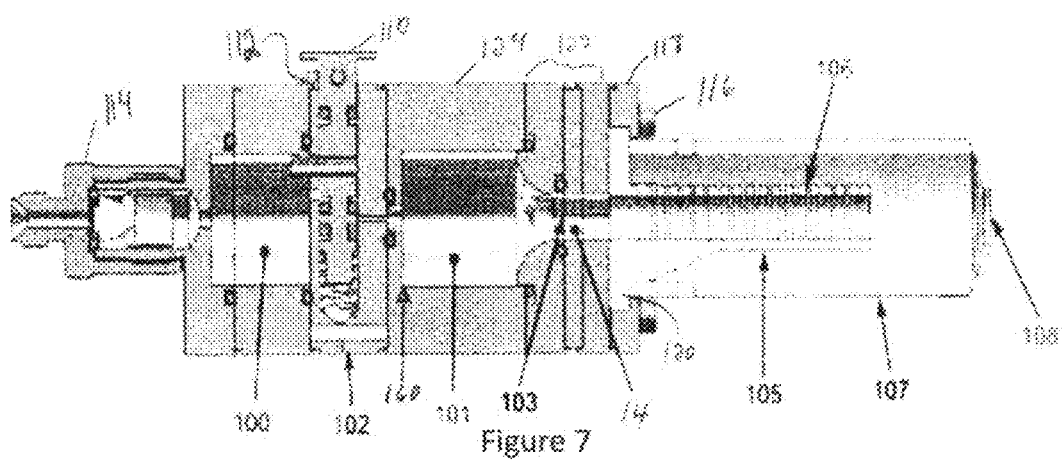
Figure 8:
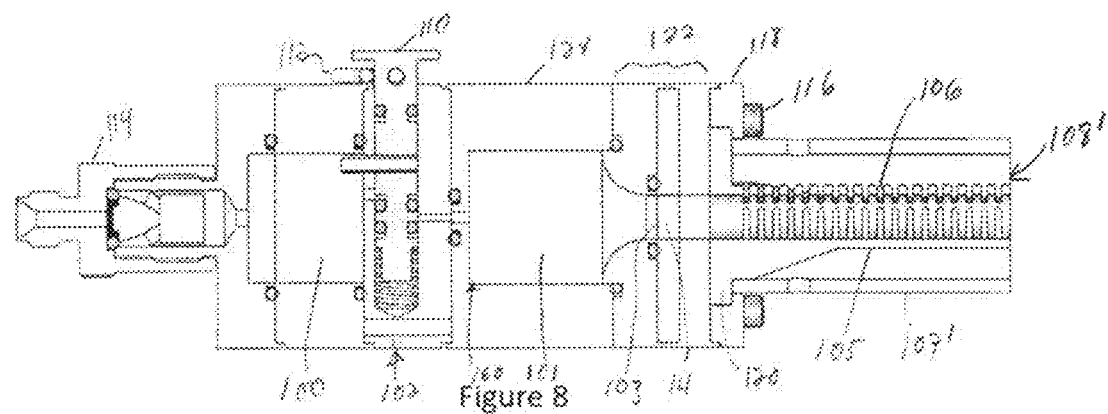
Figure 9:
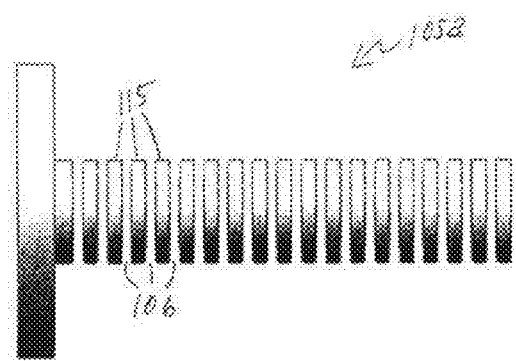
Figure 10:
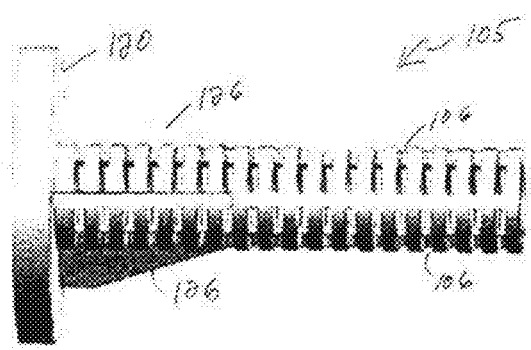
Figure 11:
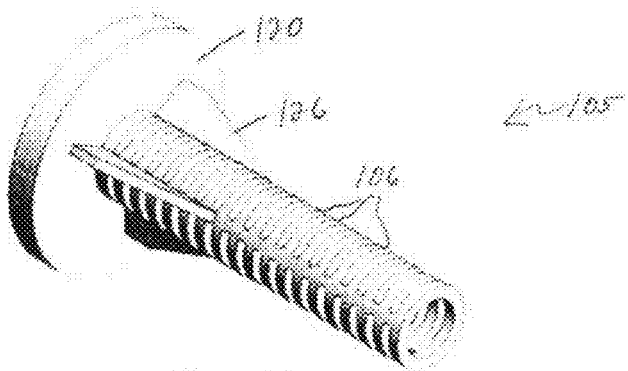
Figure 12:
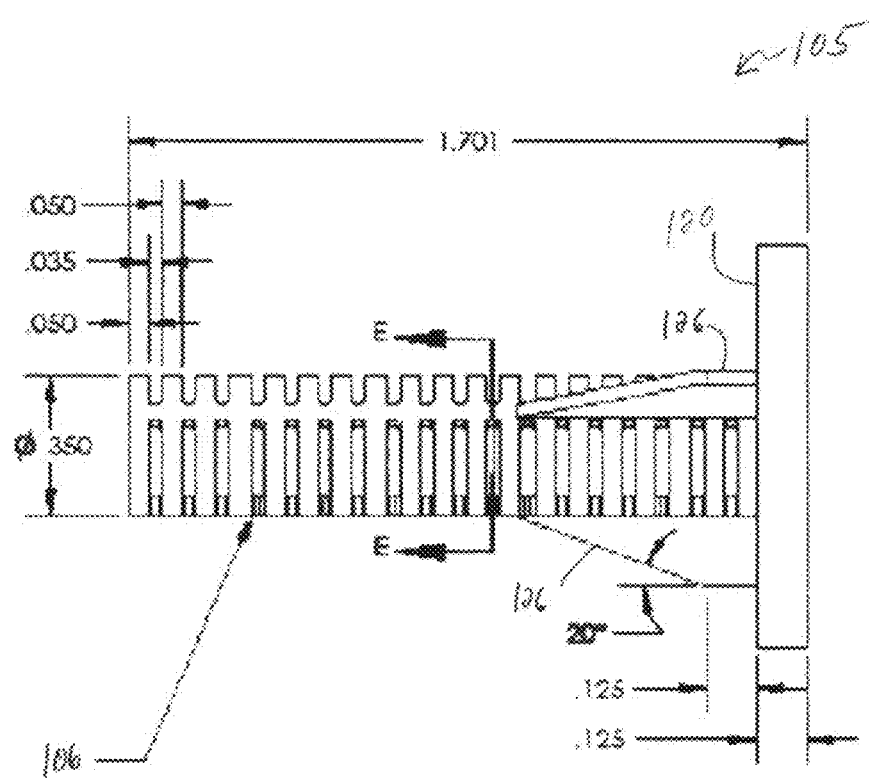
Figure 13:
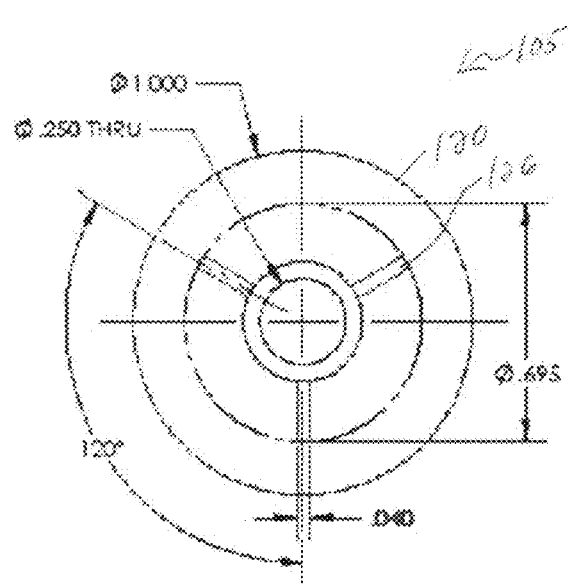
Figure 14:
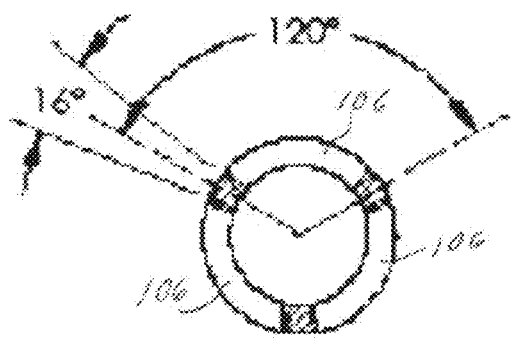

FIG. 10 is a right side elevation view of an actual cannon prototype made for the needleless syringe of FIG. 6. FIG. 11 is a front right perspective view of the cannon of FIG. 10. FIG. 12 is a left side elevation view of the cannon of FIG. 10. FIG. 13 is a front elevation view of the cannon of FIG. 10. FIG. 14 is a sectional view of the cannon of FIG. 10 taken along lines E-E of FIG. 12. Referring at once to FIGS. 10-14, the cannon 105 comprises a plurality of slots 106, the base 120 and a plurality of structural stiffeners 126. Dimensions shown on FIGS. 12-14 are expressed in inches, except for angles which are expressed in degrees. These values shown refer to an actual prototype in which the gas reservoir 100 is filled with helium at a pressure between 400 and 1000 psig, a configuration of the gas reservoir 100 and of the driver 101 providing an initial pressure in the driver 101 between 90 and 300 psig. The pressure in the gas reservoir 100 can be set between 150 and 3000 psig resulting in a pressure in the driver 101 between 50 and 1000 psig.

Any number of transversal slots 106 can cumulatively provide the desired effect; in fact, it is possible to measure the effect of a single transversal slot 106. A width of the transversal slots 106 can be set between 0.01 to 0.1 inch and simulations have been made with width values set between 0.02 and 0.08 inch. Spacing between the transversal slots 106 can be set from 0.02 inch to any larger distance or to infinite (meaning that a spacing measurement is irrelevant when a single transversal slot 106 is present). In a practical realization, an overall length of the cannon 105, as well as selected width and spacing of the transversal slots 106 determine a number of the transversal slots 106. Other dimensions and pressure values can be contemplated and may need to be adapted for a particular use and implementation. The provided values do not limit the present disclosure.

As shown, plural transversal slots 106 are positioned along a length of the cannon 105. The transversal slots 106 are arranged in groups of three (3) transversal slots 106 positioned circumferentially at a same axial length of the cannon 105, for example along line E-E of FIG. 12. Three (3) structural stiffeners 126 separate transversal slots 106 of a same group near the base 120. Without limitation, variants of the cannon 105 having for example two (2) or four (4) structural stiffeners, or ribs, and having groups of two (2) or four (4) transversal slots 106 can be contemplated.

Figure 15:
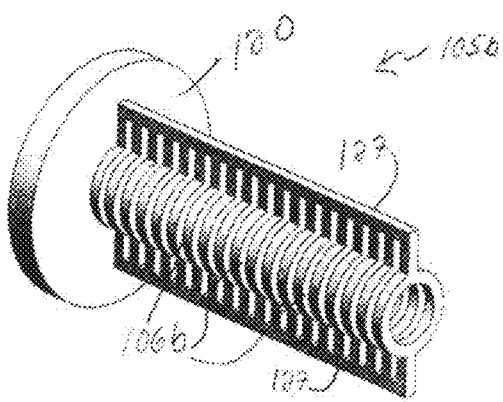

FIG. 15 is a front right perspective, partial cutaway view of a first variant of a cannon having structural stiffeners that provide defining fully circular slots. In this variant, a cannon 105b closely replicates the ideal cannon 105a by providing fully circular transversal slots 106b, two (2) or more structural stiffeners 127, or ribs, being attached to the cannon 105b, the structural stiffeners 127 being sized to allow mounting of the cannon 105b in the tube 107.

Figure 16:
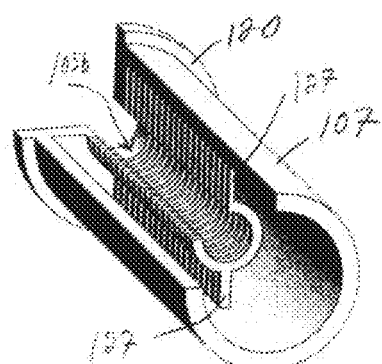

FIG. 16 is a front right perspective view of a second variant of a cannon having structural stiffeners that are imbedded in a tube. In FIG. 16, the base 120, the tube 107, and the cannon 105b and the structural stiffeners 127 of FIG. 15 are integrated in a single unitary piece.

Figure 17:
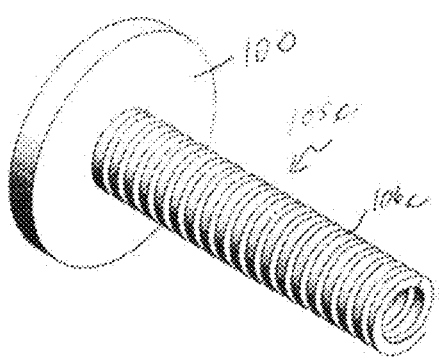
Figure 18:
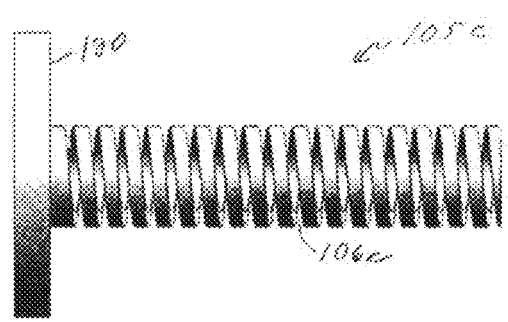

FIG. 17 is a front right perspective view of a helicoidal cannon variant. FIG. 18 is a right side elevation view of the helicoidal cannon of FIG. 17. In FIGS. 17 and 18, helicoidal cannon 105c comprises a single, continuous slot 106c forming a coil wrapped around an axis of the helicoidal cannon 105c. The continuous slot 106c extends along a full length of the cannon 105c. The continuous slot 106c is not strictly perpendicular to an axis of the cannon 105c, and not strictly perpendicular to the flow of gas within the cannon 105c, but nevertheless performs similarly as transversal slots 106 of other variants.

FIGS. 19-31 provide a theoretical basis of the operation of the needleless syringe 99, some simulation results and some experimental results obtained using a prototype of the needleless syringe 99 on human skin, ex vivo. The theoretical basis and simulation results generally apply to the various embodiments presented hereinabove. As such, in the following discussion, mentions of a "cannon 105" incorporate the cannons 105, 105b and 105c. Likewise, mentions of "transversal slots 106" incorporate the slots 106, 106b and 106c.

Figure 19:
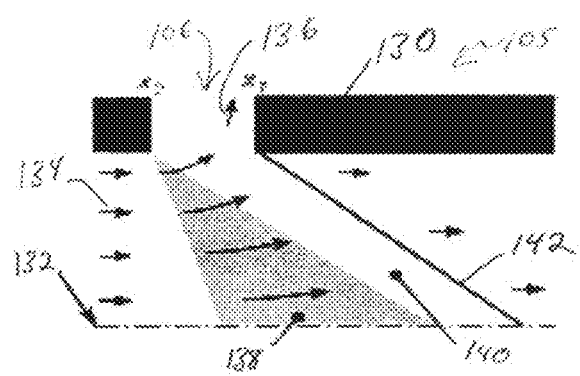

FIG. 19 is a schematic illustration of a gas flow near a transversal slot of a needleless syringe cannon. A wall 130 and a symmetry axis 132 of the cannon 105 are shown. Gas flows within the cannon 105 in a direction of arrows 134. A transversal slot 106 opens in a partial or full circumference of the wall 130 along a first line $x_0$ and closes again along a second line $x_1$, a distance between lines $x_0$ and $x_1$ forming a width of the transversal slot 106. As the flow of gas passes along the transversal slot 106, a portion 136 of the gas is expelled laterally through the transversal slot 106. This creates in the cannon 105 a gas expansion fan 138 in which gas pressure is reduced. The flow of gas is locally accelerated in the gas expansion fan 138 and a high velocity zone 140 is formed. When the gas flow reaches the second line $x_1$, an oblique shock 142 extending from the second line $x_1$ toward the axis 132 of the cannon 105 is created. The flow is directed again in parallel to the axis 132 of the cannon 105. In more details, pressure is reduced gradually within the gas expansion fan 138 and remains low within the high velocity zone 140. The flow is pressurized again by the oblique shock 142, but to a lesser extent compared to what it was before the gas expansion fan 138. As a result, an overall effect of a single transversal slot 106 in the cannon 105 is to slightly reduce the pressure of the gas flow. In the presence of multiple transversal slots 106, pressure is gradually reduced along the length of the cannon 105. In contrast, flow velocity increases gradually throughout the gas expansion fan 138 and is substantially constant within the high velocity zone 140. Flow velocity reduces again past the oblique shock 142.

Figure 20:
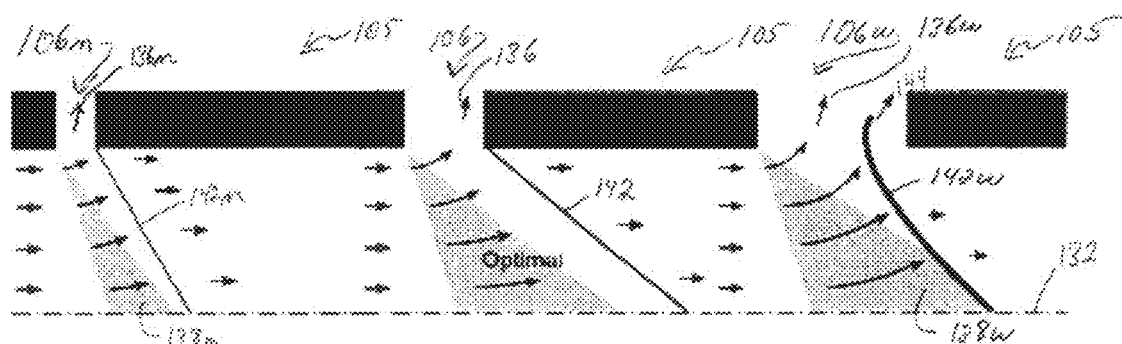

FIG. 20 schematically shows an effect of a width of the slot of the slotted cannon of a needleless syringe. Three (3) variants of the transversal slots 106 are shown. In a first variant, a narrow transversal slot 106n only allows lateral expulsion of a small portion 136n of the gas. A weak gas expansion fan 138n is created, leading to a weak local axial and radial acceleration of the flow. Since the radial acceleration is small, the flow inside the cannon 105 is not significantly deviated laterally, so a created oblique shock 142n that forms to redirect the flow back in the direction of the cannon axis 132 is also weak. Gas pressure is modestly reduced as a result of the weak gas ejection. In a second variant, an optimal transversal slot 106 allows lateral expulsion of an ideal portion 136 of the gas. Desired results expressed in the foregoing description of FIG. 19 are obtained. In a third variant, a wider transversal slot 106w allows lateral expulsion of a larger portion 136w of the gas. An expansion fan 138w is larger than in the above described variants, resulting in a larger local axial and radial acceleration of the flow and a larger pressure reduction. However, as an excessive portion 136w of the gas flow is expelled through the transversal slot 106w, the flow inside the cannon 105 is significantly deviated from the direction of the axis 132 of the cannon 105. A created oblique shock 142w is unable to properly realign the flow along the axis 132. As a result, the oblique shock 142w becomes detached from the corner $x_1$, as indicated by arrow 144. The oblique shock 142w tends to become normal to the deviated flow 144. This repositioning of the shock 142w realigns the flow along the axis 132 but results in important flow velocity losses. As it becomes normal, the oblique shock 142w locally increases the gas pressure. A large volume of gas is expelled through the transversal slot 106w and the gas pressure beyond the transversal slot 106w is in turn lower. A net result of defining an excessively wide transversal slot 106w is that the gas flow velocity is reduced overall.

Figure 21:
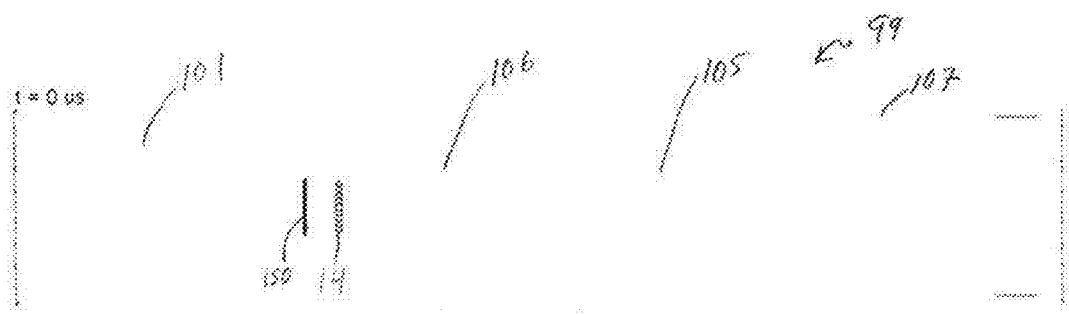
Figure 22:
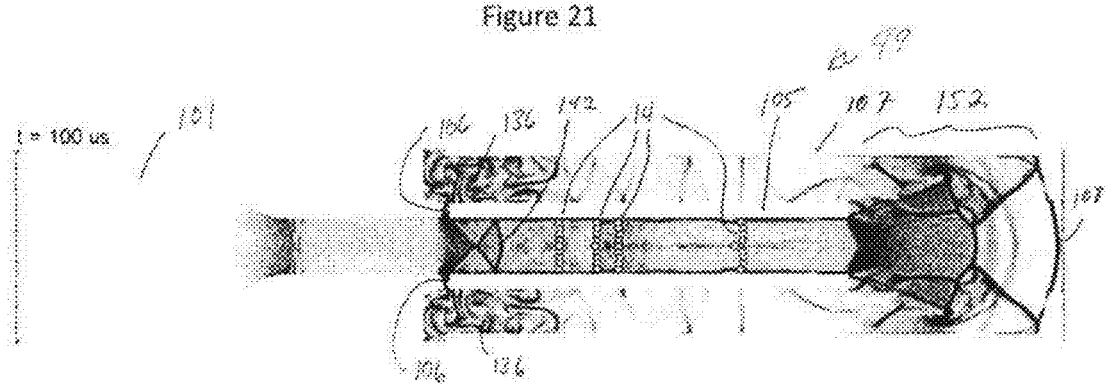
Figure 23:
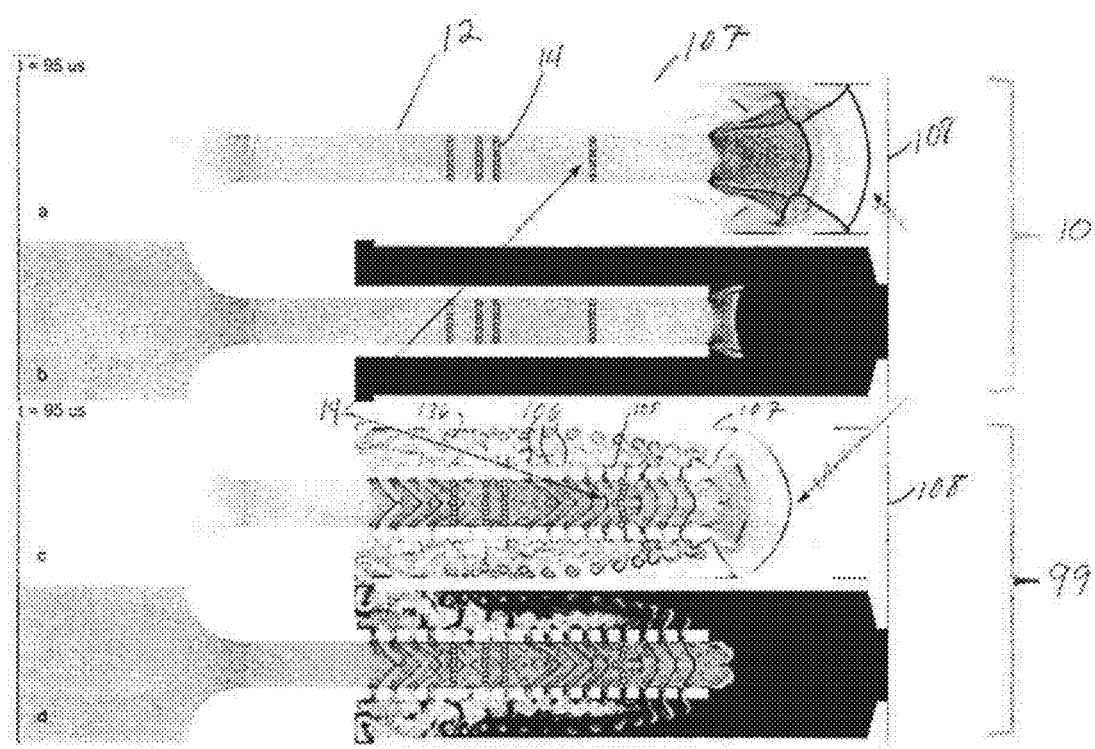
Figure 24:
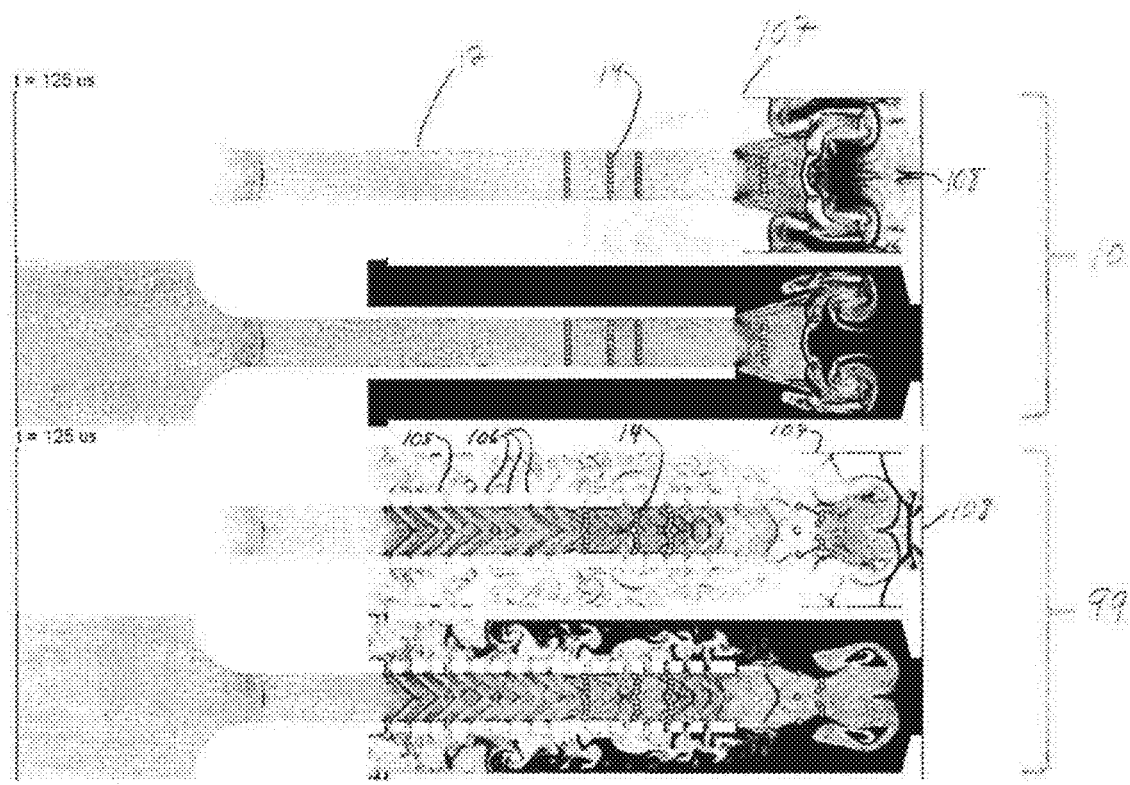
Figure 25:
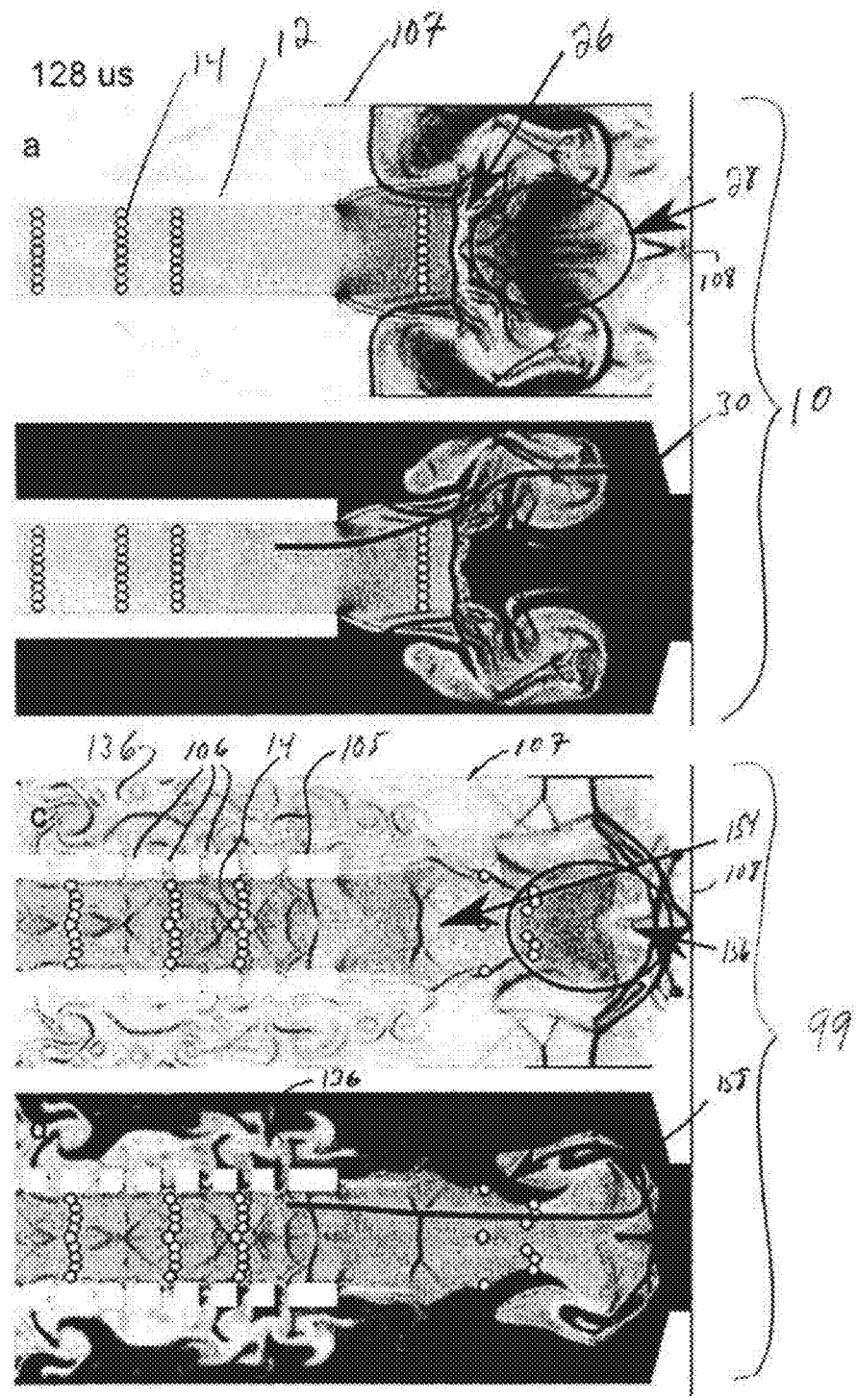
Figure 26:
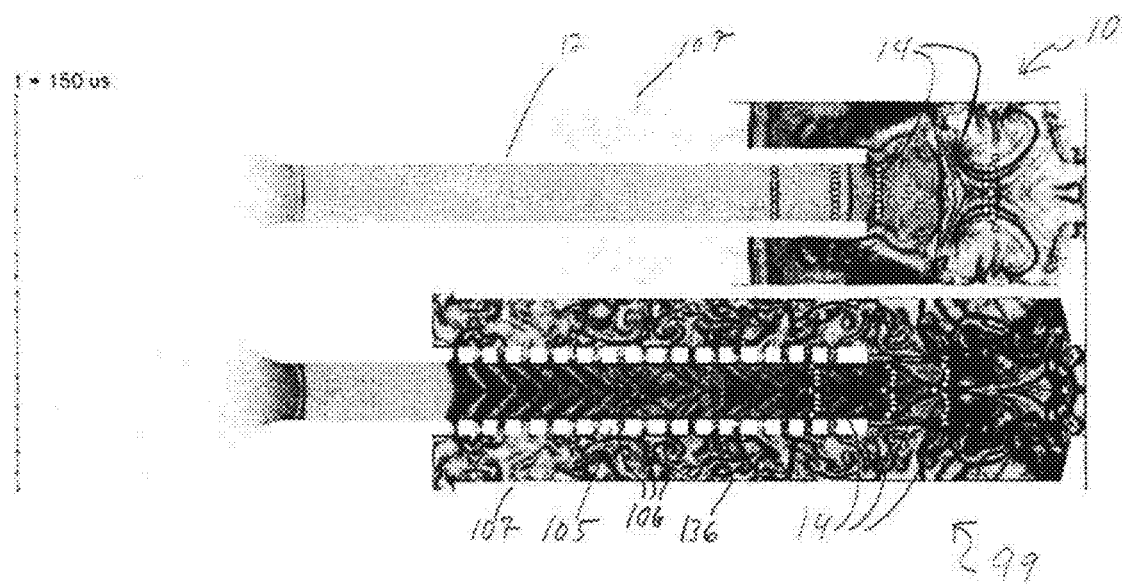
Figure 27:
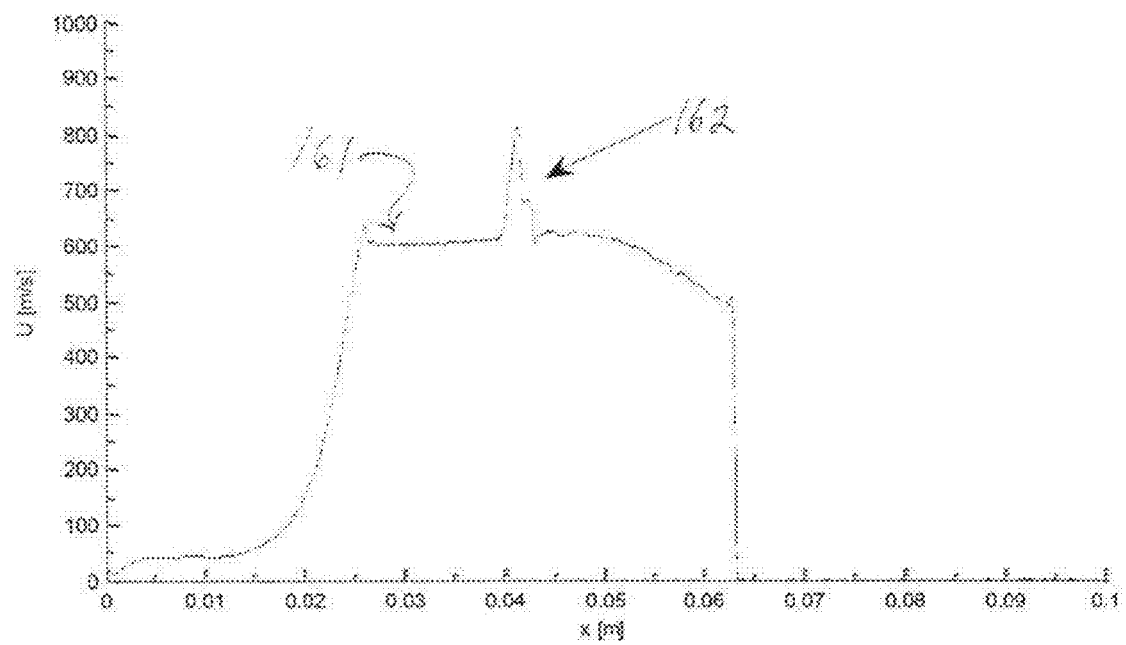
Figure 28:
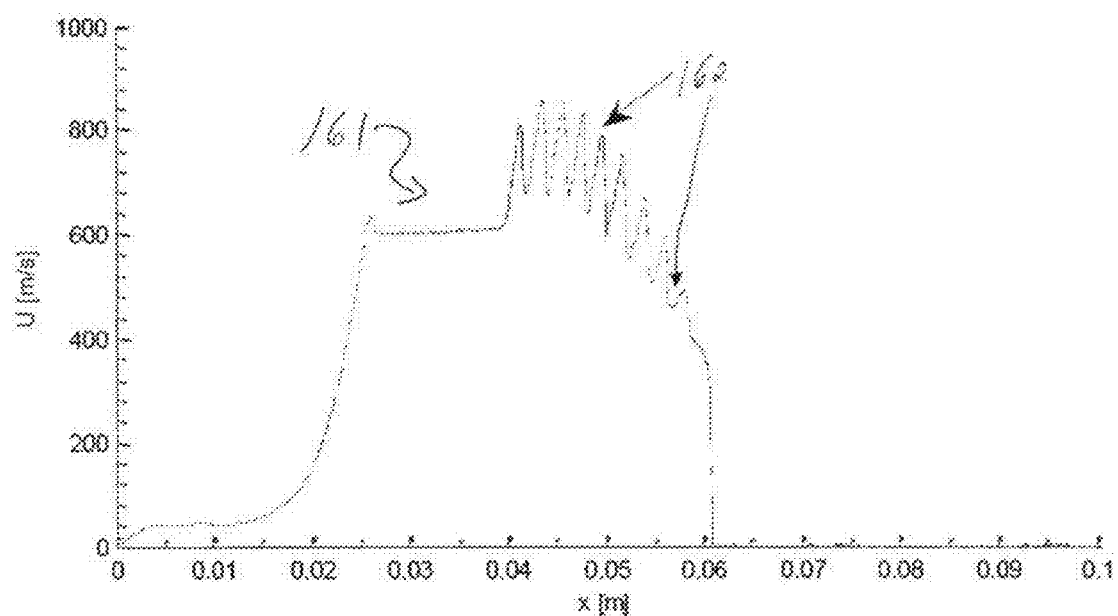
Figure 29:
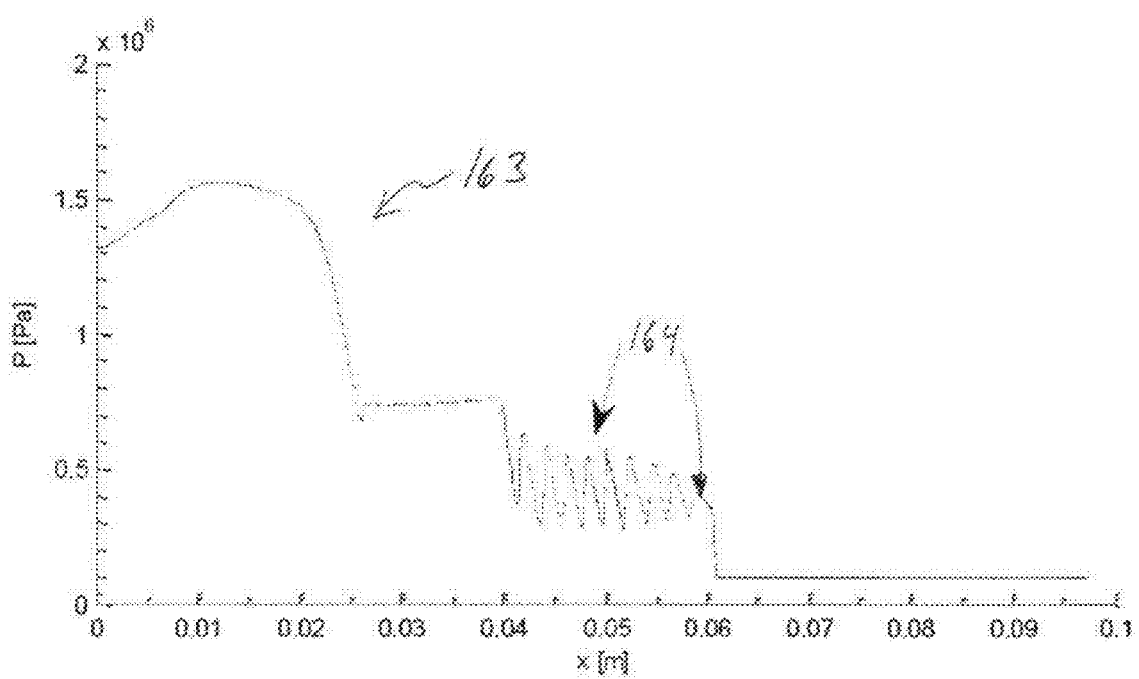

The following two Figures illustrate the effect of a single transversal slot in the cannon of a needleless syringe. FIG. 21 is a schematic representation of particles inside the needleless syringe having a cannon with a single transversal slot, at the time of release of a gas. FIG. 22 is a schematic representation of particles inside the needleless syringe of FIG. 21, at 100 µs after release of the gas. A variant of the needleless syringe 99 has a cannon 105 comprising a single transversal slot 106. A shock wave 150 is initiated at a time t=0 µs, caused by an important gas pressure discontinuity between the driver 101 and the cannon 105. Passage of the flow of gas along the transversal slot 106 creates the effect presented in the foregoing description of FIG. 19 and the therapeutic particles 14 are accelerated in the cannon 105. A portion 136 of the flow of gas is released laterally in the tube 107, or externally in embodiments without the optional tube 107. Flow density and disturbances to the flow density are reduced in an area 152 between an end of the cannon 105 and the injection site 108, this effect being minimal when the cannon 105 includes a single transversal slot 106, the effect becoming compounded in the presence of a plurality of transversal slots 106.

FIGS. 23-26 are schematic comparisons of particle movement and gas pressures within the conventional needleless syringe of FIG. 1 and within the needleless syringe of FIG. 6, at 95 μs, 125 μs, 128 μs and 150 μs after release of the gas, respectively. More specifically, FIG. 25 focuses near injection sites of the needleless syringes 10 and 99. In FIGS. 23-25, views 'a' and 'c' illustrate horizontal flow velocities (along the axis 132) in the conventional needleless syringe 10 and in the needleless syringe 99, respectively. Views 'b' and 'd' illustrate helium fraction (light areas) and air fraction (dark areas) in the conventional needleless syringe 10 and in the needleless syringe 99, respectively. While the results illustrated in FIGS. 23-26 were obtained in simulations using helium in the gas reservoir, with air being present in the tube 107, use of other gas is contemplated.

Referring at once to FIGS. 23-26, therapeutic particles 14 travel faster in the needleless syringe 99 when compared with the particles 14 in the conventional needleless syringe 10. Expulsion of portions 136 of the gas from the cannon 105 into the tube 107, through each of the transversal slots 106, reduces a gas pressure in the cannon 105. Each of the transversal slots 106 locally accelerates the flow of the gas in the cannon 105. The reduction of the gas pressure is also present, near the injection site 108. A strong stationary shock 26 and a zone of strong negative flow velocity 28 near the injection site 108 of the conventional needleless syringe 10 are replaced by a much weaker stationary shock 154 and a positive flow velocity zone 156 in the needleless syringe 99. A back flow 30 that tends to return towards a central axis of the conventional needleless syringe 10 is replaced by a flow that travels centrally towards the injection site 108 in the needleless syringe 99.

FIG. 27 is a graph showing an effect on gas flow velocity obtained from a single transversal slot on a needleless syringe cannon. The graph shows the horizontal velocity of the gas flow as a function of position measured along a path of the gas flow measured from a starting point 160, at a left hand side of the driver 101 (see arrow 160 on FIG. 7). Gas flow velocity 161 is shown at 50 μs after release of the gas. At that time, a front of the gas flow has not yet exited the cannon 105 and the gas flow velocity 161 falls to zero at about 6.4 cm from the starting point. An important local acceleration 162 of the gas flow velocity 161 is visible at about 4.0 cm from the starting point 160 where a single transversal slot 106 is located. It may be observed that, after the local acceleration 162, the gas flow velocity 161 returns to essentially the same value before the local acceleration 162.

FIG. 28 is a graph showing an effect on gas flow velocity obtained from plural transversal slots on a needleless syringe cannon. Gas flow velocity is also shown at 50 μs after release of the gas. Local increases 162 of the gas flow velocity are created as the gas flow passes by each of the transversal slots 106. Nine (9) local accelerations 162 are shown on FIG. 28 since, at 50 μs after release of the gas, a front of the gas flow has reached a ninth transversal slot 106.

FIG. 29 is a graph showing an effect on gas pressure obtained from by plural transversal slots on a needleless syringe cannon. Gas pressure 163 within the cannon 105 is shown at 50 μs after release of the gas. Local dips 164 of the gas pressure 163 are created as the gas flow passes by each of the transversal slots 106. Nine (9) local dips 164 are shown on FIG. 28 since, at 50 μs after release of the gas, a front of the gas flow has reached a ninth transversal slot 106 of the cannon 105. A net effect of these nine (9) transversal slots 106 is an overall decrease of the gas pressure 163 within the cannon 105.

FIG. 30 is a transversal microphotograph of human skin, showing a particle depth following injection using a conventional needleless syringe. A shallow penetration of particles 172 injected through a skin surface 170 into the epidermis 174 is attained in most of the cases. In comparison, FIG. 31 is a transversal microphotograph of human skin, showing a particle depth following injection using the needleless syringe of FIG. 6. A broader penetration range of the particles 172 into the epidermis 174 and into the dermis has been obtained in ex vivo experiments. Though FIG. 31 shows greater penetration depth when compared to FIG. 30, some uses of the needleless syringe 99 do not necessarily require deep penetration of therapeutic particles. The needleless syringe 99 can be configured for deep or shallow penetration, according to requirements related to a particular use.

The needleless syringe 99 implements a method for delivering therapeutic particles to a skin surface. Non-limiting examples of therapeutic particles deliverable using the needleless syringe 99 implements this method include vaccines, which may be delivered in smaller doses, with reduced risk of contamination and with less pain at an injection site, when compared to using traditional injection methods. The method for delivering therapeutic particles to a skin surface provides a gas source and a cannon having a transversal slot and places a source of therapeutic particles between the gas source and the cannon. Gas is released from the gas source to cause a propagation of the therapeutic particles through the cannon, the transversal slot being configured to locally accelerate a flow of the gas in the cannon and to reduce a pressure of the gas in the cannon. Accordingly, the gas is released from the gas source at a first pressure and exits the cannon at a second pressure lower than the first pressure. The needleless syringe 99 and the method for delivering therapeutic particles can be used to inject therapeutic particles on a patient's skin. The needleless syringe 99 can be used to perform in vivo, in vitro or ex vivo tests.

Those of ordinary skill in the art will realize that the description of the needleless syringe and method for subcutaneous delivery of therapeutic agents are illustrative only and are not intended to be in any way limiting. Other embodiments will readily suggest themselves to such persons with ordinary skill in the art having the benefit of the present disclosure. Furthermore, the disclosed needleless syringe and method may be customized to offer valuable solutions to existing needs and problems related to the operational characteristics of conventional needleless syringes.

In the interest of clarity, not all of the routine features of the implementations of needleless syringe and method are shown and described. It will, of course, be appreciated that in the development of any such actual implementation of the needleless syringe and method, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of needleless syringes having the benefit of the present disclosure.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A needleless syringe for delivering therapeutic particles, comprising:

a gas source;

a cannon having a plurality of side openings shaped as slots, the side openings being positioned along a length of the cannon and transverse to a longitudinal axis of the cannon; and a source of therapeutic particles located between the gas source and an entrance of the cannon;

wherein:

gas released from the gas source flows in the cannon and causes a propagation of the therapeutic particles through the cannon; and each opening of the plurality of side openings is configured to allow a portion of the gas to be expelled laterally from the cannon, causing a corresponding local reduction of a pressure of the gas in the cannon and causing a corresponding local acceleration of a flow of the gas in the cannon, so that the pressure and a velocity of the gas in the cannon gradually decrease as the gas flows beyond successive ones of the side openings.

2. The needleless syringe as defined in claim 1, comprising a puncturable membrane for releasably sealing the gas source.

3. The needleless syringe as defined in claim 2, comprising a gas reservoir, a valve and a driver, wherein opening of the valve releases the gas from the gas reservoir into the driver, a pressure of the gas in the driver causing a puncture of the membrane.

4. The needleless syringe as defined in claim 1, comprising a tube surrounding the cannon, the tube having an internal diameter sufficient for allowing release of gas from the cannon through the side openings, an end of the tube opposite from the gas source forming an injection site.

5. The needleless syringe as defined in claim 4, wherein the end of the tube opposite from the gas source extends beyond an extremity of the cannon.

6. The needleless syringe as defined in claim 1, wherein passage of the flow of the gas along each of the side openings creates a gas expansion fan within the cannon.

7. The needleless syringe as defined in claim 1, wherein the plurality of side openings comprise one or more groups of slots, each group comprising two or more slots positioned circumferentially at a same axial length of the cannon.

8. The needleless syringe as defined in claim 1, wherein the plurality of side openings comprises circular slots, the cannon being supported by at least a pair of structural stiffeners connected to the cannon between the circular slots.

9. A method for delivering therapeutic particles to a skin surface, comprising:

providing a gas source;

providing a cannon having a plurality of side openings shaped as slots, the side openings being positioned along a length of the cannon and transverse to a longitudinal axis of the cannon;

placing a source of therapeutic particles between the gas source and an entrance of the cannon; and releasing gas from the gas source to cause the gas to flow in the cannon and to cause a propagation of the therapeutic particles through the cannon;

wherein each opening of the plurality of side openings allows a portion of the gas to be expelled laterally from the cannon, causing a corresponding local reduction of a pressure of the gas in the cannon and causing a corresponding local acceleration of a flow of the gas in the cannon, so that the pressure and a velocity of the gas in the cannon gradually decrease as the gas flows beyond successive ones of the side openings.

10. The method as defined in claim 9, wherein the gas is released at a first pressure and wherein the gas exits the cannon at a second pressure lower than the first pressure.

11. Use of the method as defined in claim 9 on a patient's skin.

12. Use of the method as defined in claim 9 in vitro.

13. Use of the method as defined in claim 9 ex vivo.

* * * * *